United States Patent [19]

Smock et al.

[11] Patent Number: 5,390,535
[45] Date of Patent: Feb. 21, 1995

[54] DROP TEST DEVICE

[75] Inventors: Daniel D. Smock, Highand; Leslie R. Parry, Harrison Township, both of Mich.

[73] Assignee: Detroit Testing Laboratory, Inc., Warren, Mich.

[21] Appl. No.: 217,984

[22] Filed: Mar. 25, 1994

[51] Int. Cl.$^6$ ............................................. G01N 3/00
[52] U.S. Cl. ....................................................... 73/79
[58] Field of Search ...................... 73/79, 12.04, 12.06

[56]         References Cited
         U.S. PATENT DOCUMENTS

| 161,737 | 4/1975 | Beardslee. | |
|---|---|---|---|
| 1,491,990 | 4/1924 | Kindervater | 73/15 |
| 2,740,286 | 3/1956 | De Vost et al. | 73/12.04 |
| 3,426,578 | 2/1969 | Bergs et al. | 73/12 |
| 3,888,108 | 6/1975 | Brands | 73/12 |
| 3,946,598 | 3/1976 | Towne et al. | 73/67.1 |
| 4,020,672 | 5/1977 | Safford | 73/12.04 |
| 4,856,319 | 8/1989 | Hogan et al. | 73/12 |

FOREIGN PATENT DOCUMENTS 2334096  7/1977  France ............................... 73/12.04

Primary Examiner—Richard E. Chilcot, Jr.
Assistant Examiner—Harshad Patel
Attorney, Agent, or Firm—Reising, Ethington, Barnard, Perry & Milton

[57]         ABSTRACT

A drop test apparatus (10) for testing the resiliency of playground surfaces (12) includes a drop module (14) and a release mechanism (16) for holding the drop module (14) at an elevated reference height and releasing the drop module (14) to fall to the surface (12). Vertically-extending guide elements (18) guide and maintain the drop module (14) in a constant attitude from release until surface (12) impact. A support structure (24) extends between the guide element's upper (20) and lower (22) ends and holds the guide element (18) in a generally vertical orientation above the surface (12). Both the guide element (18) and support structure (24) comprise a plurality of interconnecting collapsible and disassemblable parts allowing a single person to rapidly convert the support structure (24) and the guide element (18) between the operational surface-testing configuration and a compact configuration for convenient transport.

19 Claims, 4 Drawing Sheets

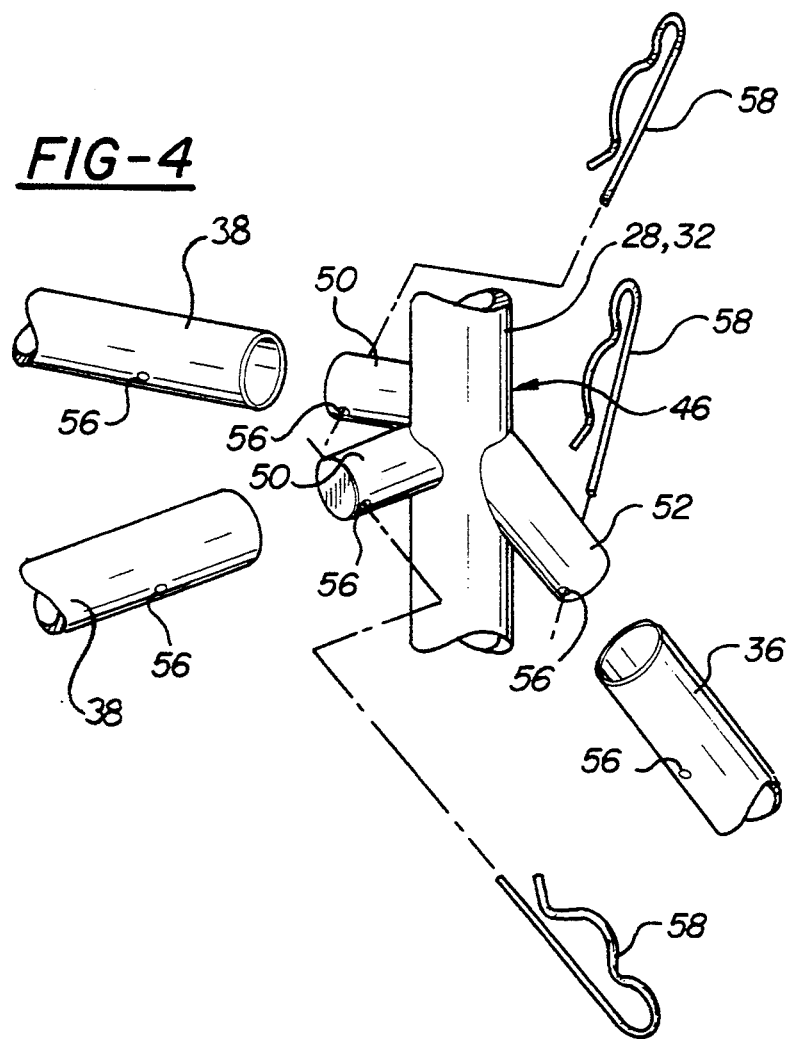
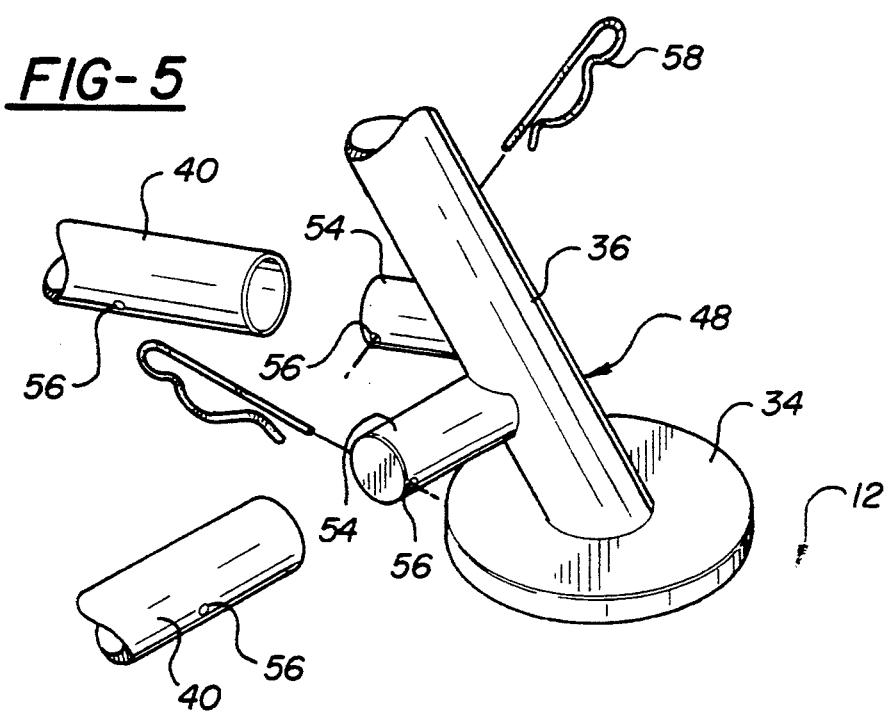

DROP TEST DEVICE

TECHNICAL FIELD

This invention relates to devices for testing the resiliency or hardness of playground surfaces.

BACKGROUND OF THE INVENTION

Playground surfacing must be reasonably safe for children. The Consumer Product Safety Commission (CPSC) Handbook for Public Playground Safety contains a surface-testing standard called a Maximum Head Injury Coefficient (Max HIC). To properly determine if a surface's HIC meets the Max HIC standard, the surface must be tested in accordance with ASTM F1292-93, Standard Specification for Impact Attenuation of Surface Systems Under and Around Playground Equipment and per ASTM F355-86, Standard Test Method for Shock-Absorbing Properties of Playing Surface Systems and Materials.

As playground surfacing can not be reliably tested in a laboratory, portable field testing equipment is often required, i.e., test equipment that is capable of providing consistent test results in accordance with the CPSC and ASTM standards. To test within these requirements testing personnel employ a linear accelerometer transducer embedded in a metal headform. The testing personnel drop the accelerometer transducer and headform from the specified reference height to the playground surface. Normally electrical wires transmit the raw accelerometer data from the accelerometer transducer to a separate data processing unit which calculates the HIC.

To get consistent reproducible data, the headform must strike the surface in such a way that the linear accelerometer axis is within plus or minus 5 degrees of vertical. Also, the headform must drop from a stationary condition to avoid imparting random accelerations to the headform and skewing the test data. Also, there must be something to support the headform in that stationary condition at varying heights up to 12 feet as specified in ASTM F1292-93.

Current surface-testing systems either use guide elements to guide the headform to impact or comprise hand-released headforms that fall without guidance.

Current systems using flexible guide elements also include some form of rigid support structure that vertically supports the guide elements. Some systems have semi-collapsible support structures, but with rigid guide elements. In any event, all known systems using guide elements either have rigid, non-collapsible support structures or rigid, non-collapsible guide elements. For this reason, these systems are difficult to disassemble, transport and reassemble for field testing.

For example, U.S. Pat. No. 3,426,578 to A. Bergs et al., issued Feb. 11, 1969 discloses an impact testing apparatus for conducting controlled attitude tests. The apparatus includes a drop module, a release means, a pair of guide cables and a support structure that holds the guide elements in a generally vertical orientation. With this design, the test specimen is the drop module rather than the impact surface. The Bergs '578 patent, therefore, includes an impact base positioned on a permanent foundation. Consequently, the Bergs '578 patent's support structure is permanent and not designed for transport.

An example of a transportable system is disclosed in French Patent Number 2,334,096. This patent discloses a portable drop-test device for testing road surfaces with a surface penetrator. The system includes a drop module and a release means. The system has a semi-collapsible support structure with a rigid central guide element. The support structure includes three legs assembled and joined together with cross braces by way of removable wing-nut and bolt fasteners. When unbolted, the support structure is inwardly collapsible onto the rigid guide element much in the same manner as a camera tripod. This allows an operator to reduce the overall diameter of the system for transport, but not its length.

Hand-released headform systems are easy to transport but are difficult to manually release without imparting random translational or rotational loads to the headform. For example, U.S. Pat. No. 4,856,318 issued to Hogan et al. on Aug. 15, 1989 discloses a hand-carried, hand-released transducer module. To comply with ASTM F355-86 an individual must climb a ladder or a piece of playground equipment, then attempt to manually hold the module at the exact reference height and release it without imparting any significant translational or rotational loads.

SUMMARY OF THE INVENTION AND ADVANTAGES

The present invention is a drop test apparatus for testing the resiliency of playground surfaces. The apparatus comprises a drop module and release means for holding the drop module at an elevated reference height and releasing the drop module to fall to the surface. A guide element extends between an upper end and a lower end in an operational configuration for guiding and maintaining the drop module in a constant attitude from release until surface impact. A support structure extends between the upper and lower ends of the guide element in an operational configuration for holding the guide element in a generally vertical orientation above the surface. Characterizing the apparatus are conversion means for rapidly converting each of the support structure and the guide element between the operational configuration for surface-testing and a compact configuration for convenient transport.

The present invention holds its drop module motionless and at the precise specified reference height above the surface prior to a drop. At the same time, the invention is easy for a single person to disassemble, transport and reassemble for field testing. Because it collapses in both width and length the invention fits in a container small enough to carry in a delivery vehicle the size of a station-wagon or mini-van.

BRIEF DESCRIPTION OF THE DRAWINGS

To better appreciate the advantages of this invention, please refer to the following detailed description in connection with the accompanying drawings:

FIG. 4 is an exploded perspective view of an upper pinned joint;

FIG. 5 is an exploded perspective view of a lower pinned joint;

DETAILED DESCRIPTION OF THE PREFERRED EMBODIMENT

Figure 1:
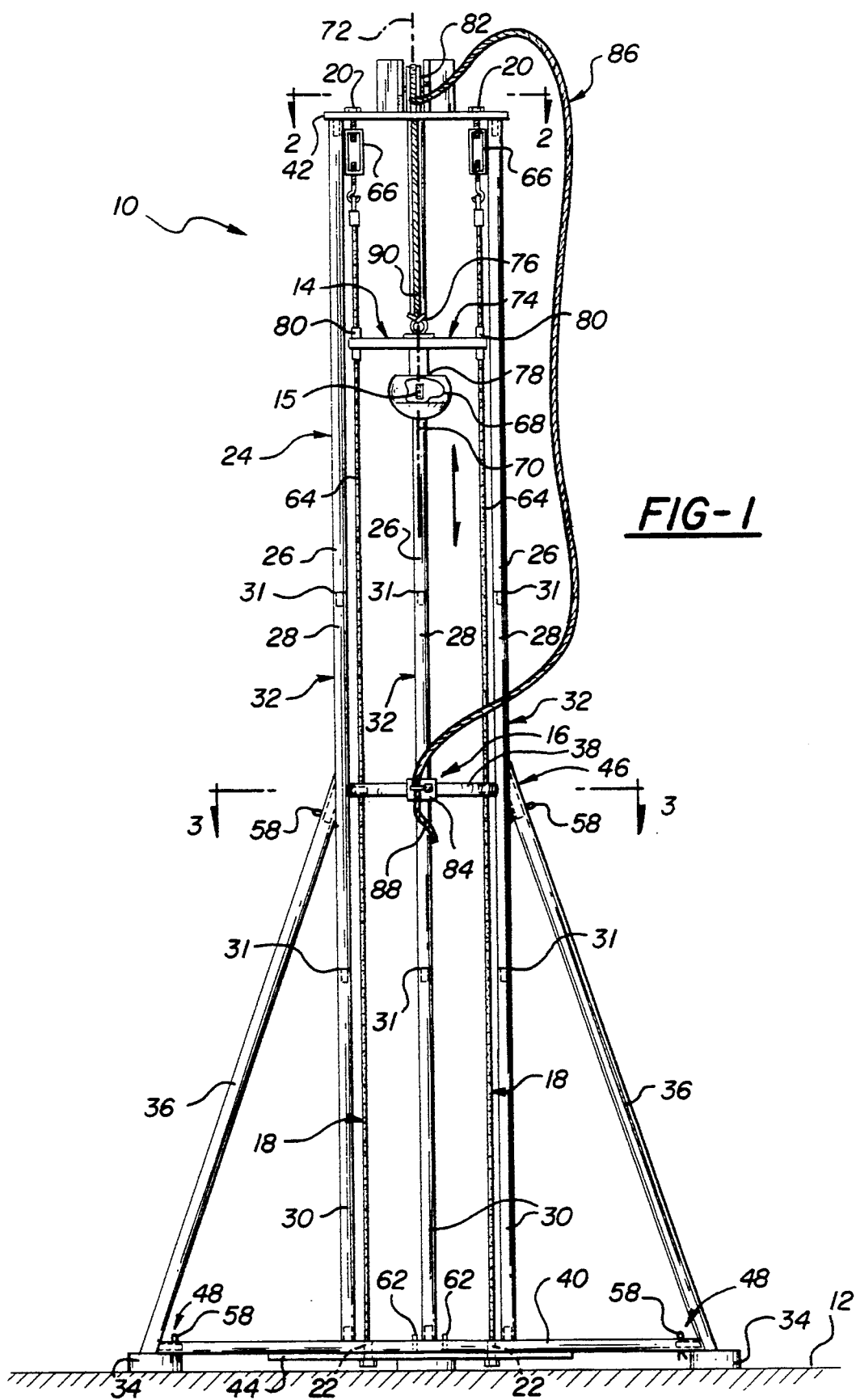
FIG. 1 is a side view of the invention in its operational configuration with the rope drawn away for clarity.

The invention, generally shown at 10 in FIG. 1, is an apparatus for testing the resiliency or hardness of playground surfaces 12. The apparatus 10 includes a drop module 14 for carrying a linear accelerometer transducer 15 and a release mechanism 16 for holding the drop module 14 at an elevated reference height and releasing the drop module 14 to fall to the surface 12. The apparatus 10 also includes guide elements 18 with upper 20 and lower 22 ends. The guide elements 18 guide and maintain the drop module 14 in a constant attitude from release until surface 12 impact. A support structure 24 extends between the guide elements' upper 20 and lower 22 ends when the apparatus 10 is in its operational (testing) configuration. The support structure 24 holds the guide element 18 in a generally vertical orientation above the surface 12. The apparatus 10 includes conversion means for enabling a single test person to rapidly assemble both the support structure 24 and the guide elements 18 into their operational configuration for surface-testing. After testing, the conversion means enables the test person to single-handedly disassemble and collapse both the support structure 24 and guide element 18 and pick the disassembled parts into a compact configuration for convenient transport.

Except where it indicates otherwise, the following text describes the preferred embodiment in its operational configuration, i.e., assembled for testing a surface 12.

The support structure 24 includes upper 26, center 28 and lower 30 vertical segments, as is best shown in FIG. 1. In the apparatus' 10 operational configuration, the vertical segments 26, 28, 30 have connections 31 where they releasably join into generally vertical rods 32. In the preferred embodiment there are three vertical rods 32 disposed equidistant from and parallel to each other. The upper 26 and center 28 vertical segments' lower ends are narrowed for insertion into the center 28 and lower 30 vertical segments' upper ends, respectively. In other words, the vertical segments 26, 28, 30 join together at connections 31 in much the same manner as tubular steel tent poles or canopy supports.

The support structure 24 also includes three feet 34, best shown in FIG. 5, disposed in a triangular pattern on the surface 12. In the preferred embodiment, the feet 34 are circular steel disks. Three leg segments 36 extend diagonally between the feet 34 and the vertical rods 32 and are fixedly connected to the feet 34. The leg segments 36 each releasably connect to one of the vertical rods 32 and serve to support the apparatus 10 against tipping forces.

Figure 3:
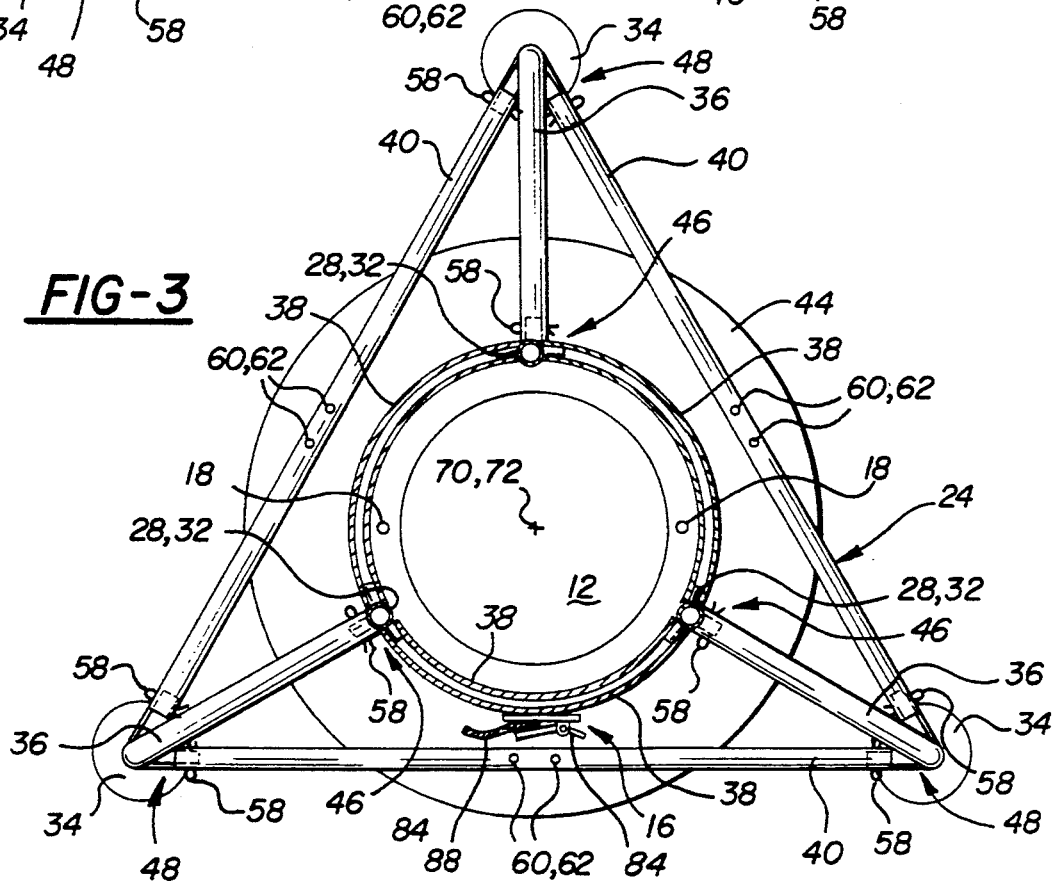
FIG. 3 is a cross-sectional view taken along line 3—3 of FIG. 1.

Referring to FIG. 3, upper horizontal segments 38 extend between and releasably connect to the vertical rods 32. In the preferred embodiment the upper horizontal segments 38 curve outwardly and avoid conflicting with the drop module's 14 path. The upper horizontal segments 38 may be any shape or configuration that avoids interference with the drop module 14 as it travels along the guide elements 18.

Figure 2:
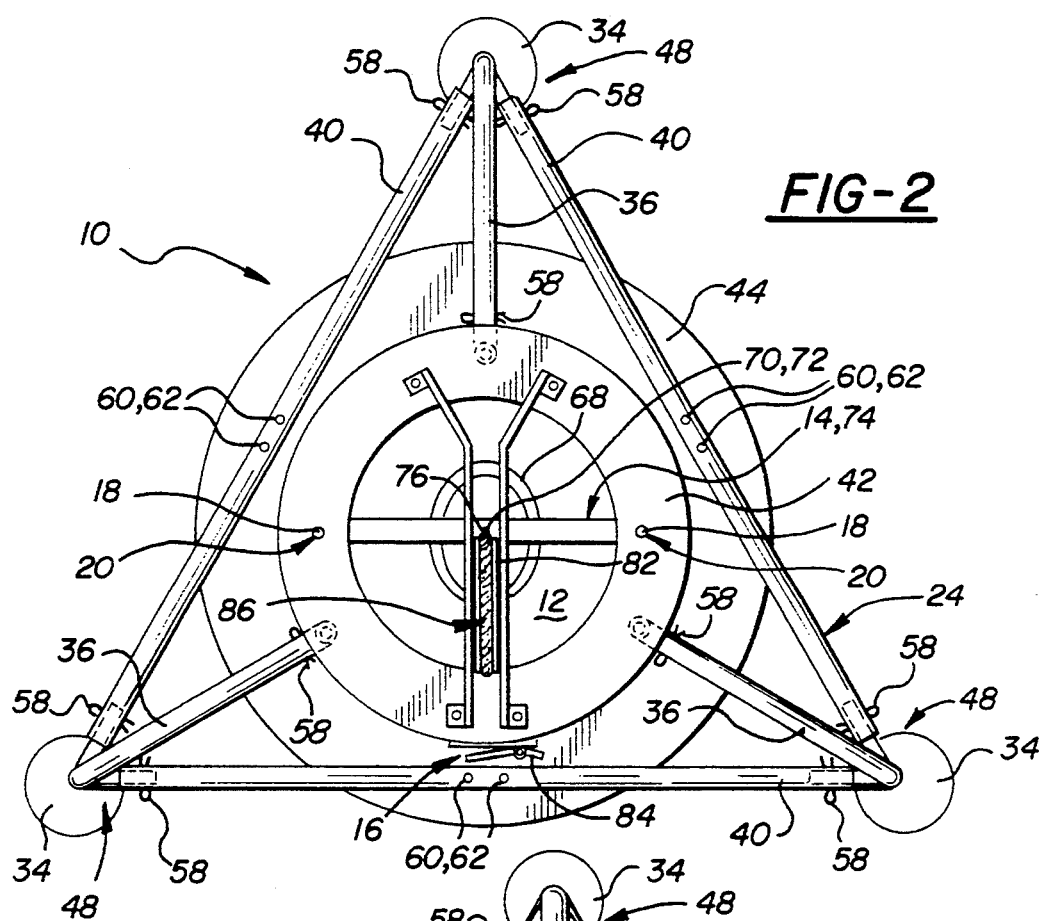
FIG. 2 is a top view taken along line 2—2 of FIG. 1.

As is best shown in FIG. 2, lower horizontal segments 40 extend between and releasably connect the legs 36 to provide additional stability. In the preferred embodiment, the vertical 32, horizontal 38, 40 and leg 36 segments all comprise tubular steel.

Figure 6:
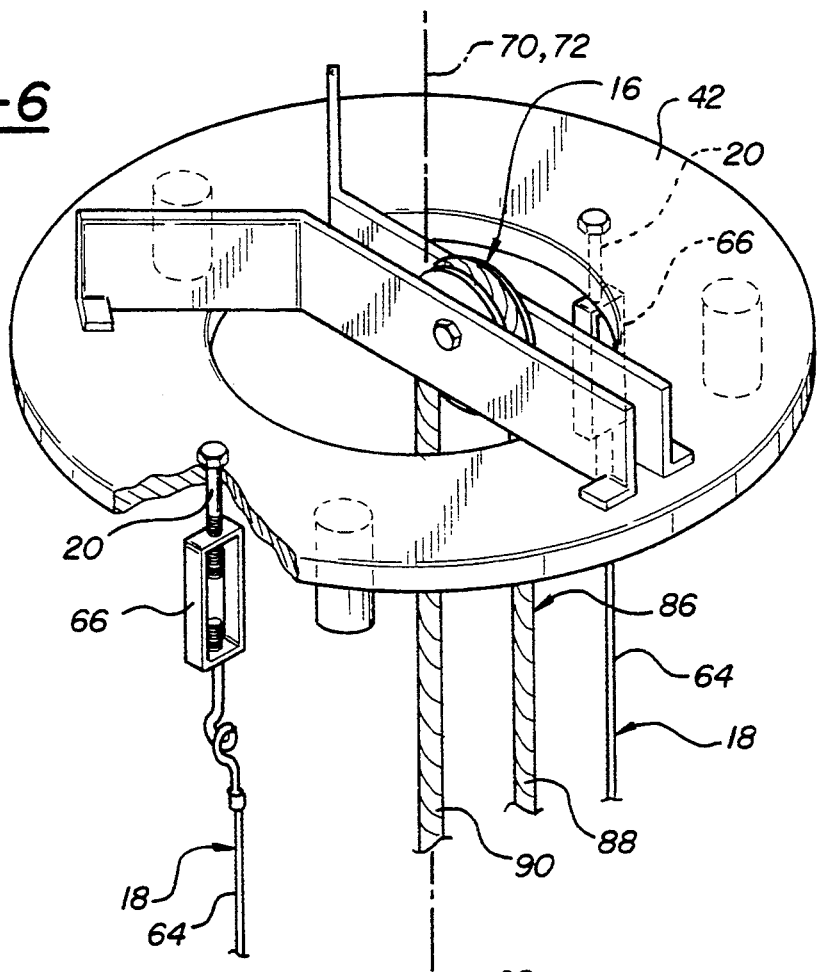
FIG. 6 is a perspective view of the top plate and pulley, partially broken away to show the turnbuckle.
Figure 7:
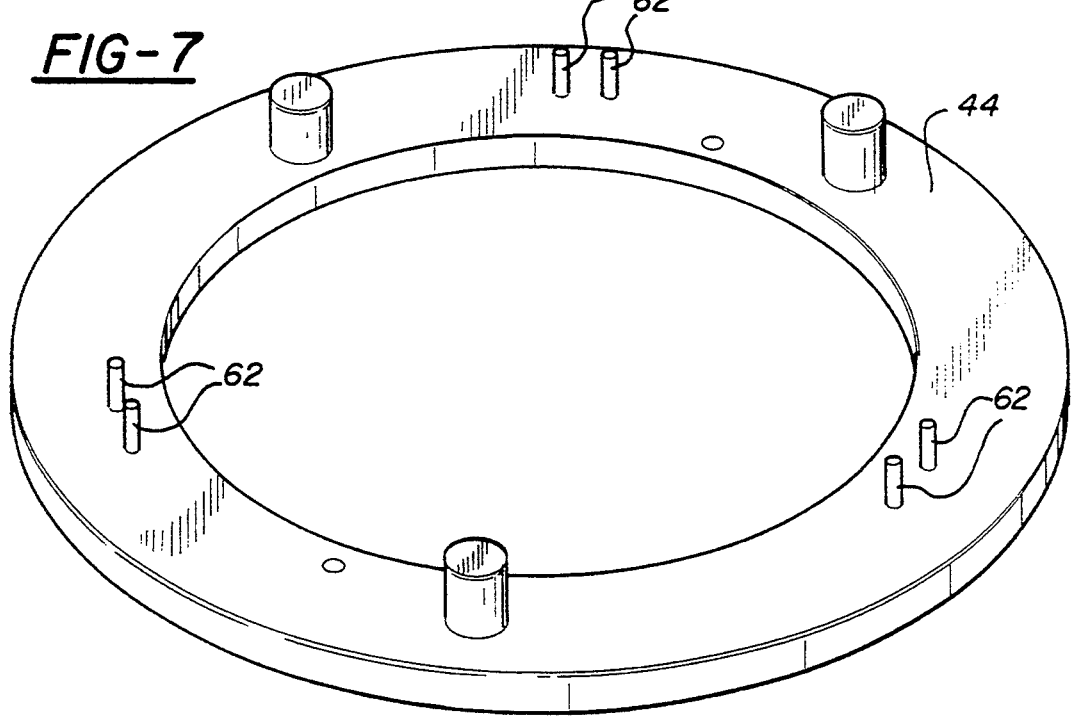
FIG. 7 is a perspective view of the bottom plate.

The support structure 24 has a top plate shown at 42 in FIG. 6, and a bottom plate, shown at 44 in FIG. 7. In the preferred embodiment, the top plate 42 and bottom plate 44 comprise flat annular steel plates. However, the plates 42, 44 can have other shapes.

The vertical rods 32 are rigidly and releasably connected at each of their distal ends to the top plate 42 and the bottom plate 44.

The conversion means includes upper pinned joints, generally indicated at 46 in FIG. 4, and lower pinned joints, generally indicated at 48 in FIG. 5. Each upper pinned joint 46 includes two horizontal solid posts 50, and one diagonal solid post 52 rigidly fixed to a center vertical segment's 28 approximate longitudinal midpoint. At each upper joint 46, the horizontal posts 50 extend radially outwardly and parallel to the surface 12 to engage the upper horizontal segments 38. The diagonal post 52 at each upper joint 46 extends diagonally downwardly for engaging the leg segments' 36 open upper ends.

The lower pinned joints 48 include two lower solid posts 54 rigidly fixed to each leg segment 36 just above each foot 34. The lower posts 54 extend outwardly from each leg segment 36 and parallel to the surface 12 for engaging the lower horizontal segments' 40 open ends.

The posts 50, 52, 54 have diameters small enough to allow sliding removable insertion into their corresponding segments' 36, 38, 40 ends. Each of the pinned joints 46, 48 includes quick-release pin holes 56 for receiving quick release pins The quick-release pin holes 56 extend through the segments' 36, 38, 40 ends and the posts 50, 52, 54 The quick release pins 58 are made of steel wire and are shaped to allow easy insertion and removal while providing a secure lock .in the joints 46, 48 they are inserted through. The quick release pins 58 secure the joints 46, 48 by preventing the posts 50, 52, 54 and corresponding segments' 36, 38, 40 ends from moving longitudinally in relation to each other.

As is best shown in FIGS. 2 and 3, each of the lower horizontal segments' 40 center portions are disposed adjacent and above the bottom plate's 44 outer circumference. The lower horizontal segments 40 each have two vertical pin holes 60 drilled midway along their lengths. The vertical pin holes 60 receive fixed pins 62 extending vertically upward from the bottom plate's 44 outer circumference, best shown in FIG. 7. In the preferred embodiment the fixed pins 62 are welded to the bottom plate 44 but may be permanently affixed by other means common in the metal-working art. In other embodiments, the fixed pins 62 may be bonded to the horizontal segments with the pin-receiving holes disposed in the bottom plate 44.

The conversion means may include a support structure 24 that is completely or partially collapsible rather than being disassemblable as in the present embodiment. In other words, portions of the support structure may telescope or scissor into a compact configuration.

The conversion means also operates to collapse the guide elements 18. In the preferred embodiment, the guide elements 18 comprise two flexible elongated members 64. More specifically, in the preferred embodiment, the guide elements 18 comprise twisted-wire steel cable 64.

Referring to FIG. 1, the guide elements 18 have top ends 20 and bottom ends 22 with the top ends 20 releasably attached to the top plate 42 and the bottom ends 22 releasably attached to the bottom plate 44. The guide elements 18 may be attached to the top 42 and bottom 44 plates by any of a number of means commonly used for attaching cables 64 to flat plates.

The flexible elongated members 18 have tightening mechanisms 66 for tensioning and straightening the flexible elongated members 18. The tightening mechanisms 66 also allow the flexible elongated members to compressively hold the vertical rods 32 together. In other words, the flexible elongated members' 64 compressive holding capability obviates any need for pins or other securing devices to prevent the vertical rods 32 from falling apart. In the preferred embodiment, the tightening mechanisms 64 comprise turnbuckles.

The guide elements 18 need not be flexible, but may rather comprise disassemblable, telescoping, scissoring or otherwise collapsible rigid members.

The drop module 14 includes a steel headform 68 which carries a linear accelerometer transducer 15. While the headform 68 may be one of any of a number available for surface resiliency testing, the preferred embodiment uses the 'C' Size ANSI metal headform for ASTM Procedure C, Test Method F355. The accelerometer transducer 15 has a sensitive axis 70 aligned generally parallel to and coincident with the path the headform's 68 impact point follows as it falls to the surface 12, i.e., the drop axis 72. In the preferred embodiment, the drop axis 72 is disposed between the three vertical rods 32, is parallel to the vertical rods 32 and is approximately equidistant from the vertical rods 32. The accelerometer transducer's sensitive axis 70 is aligned within five 5 degrees of vertical in accordance with ASTM Test Method F355.

The drop module 14 also includes a carriage assembly 74 with an upper attach point 76 and a lower attach point 78. The upper 76 and lower 78 attach points are disposed along a vertical axis passing through the drop module's 14 combined center of gravity and generally coincident with the drop axis 72. The headform 68 is rigidly attached to the lower attach point 78 and the release means 16 is connected to the upper attach point 76.

Two loose guide tubes 80 slidably support the drop module 14 on the flexible elongated members 64. Each of the loose guide tubes 80 is concentrically and slidably disposed around one of the flexible elongated members 64. The loose guide tubes 80 may contain replaceable bushings formed of materials such as bronze, nylon, TEFLON or the like to control friction and wear of the tubes 80 and the flexible elongated members 64.

The release mechanism, best shown at 16 in FIG. 1, includes a pulley 82 rotatably attached to the top plate 42, a mechanical release 84 disposed on the support structure 24, and a rope 86 disposed over the pulley 82. The rope 86 has a rope first end 88 for releasably engaging the mechanical release 84 and a rope second end 90 tied or otherwise connected in some manner to the drop module 14.

Referring to FIG. 6, the rope second end 90 extends tangentially from the pulley 82 along the drop axis 72 to the drop module 14. Referring back to FIG. 1, the rope first end 88 is releasably attached to the mechanical release 84. In the preferred embodiment, the mechanical release 84 is fixed to the upper horizontal segment 38 that is radially disposed closest to a position directly beneath the pulley 82. Please note that In FIG. 1 the rope first end 88 is drawn away from the rest of the apparatus 10 for clarity only. In the preferred embodiment, the actual routing of the rope first end 88 is downward from the pulley 82, through the annular opening in the top plate 42 and downward to the mechanical release 84.

To assemble the apparatus 10, an assembler joins the vertical rods 32 together and joins them to the top 42 and bottom 44 plates. The assembler then threads the cables 64 through the drop module 14 guide tubes 80 and attaches the guide elements' ends 20, 22 to the top 42 and bottom 44 plates. The assembler then turns the turnbuckles 66 until the cables 64 are taut. The assembler next installs the upper and lower horizontal segments 40, the leg segments 36, and inserts the quick-release pins 58 into the upper 46 and lower 48 pinned joints. After threading the rope 86 through the pulley 82 and standing the apparatus 10 on its feet 34, the assembler ties the rope second end 90 to the drop module 14 and connects any data-transmitting wire leads to the headform 68. Once the assembler raises the drop module 14 to a reference height and connects the wire leads to data processing instruments, the apparatus 10 is ready for testing.

Disassembly is a straight-forward reversal of the assembly process. A disassembler first disconnects any wire leads from the headform 68. The disassembler then lays the apparatus 10 on its side and pulls the quick-release pins 58 from the upper 46 and lower 48 pinned joints. The disassembler then removes the upper and lower horizontal segments 40 and leg segments 36. The disassembler then loosens the turnbuckles 66 until there is sufficient cable slack to pull the vertical rods 32 apart. After disassembly, the disassembler packs the pieces in a packing crate, and loads the crate into a vehicle for transport.

I intend the above terminology to illustratively describe the invention's preferred embodiment and not to limit the invention's scope.

Obviously, many modifications and variations of this invention are possible in light of the above teachings. Within the scope of the appended claims, in which reference numerals are merely for convenience and are not limiting, one may practice the invention other than as the above specification describes.

I claim:

1. A drop test apparatus (10) for testing the resiliency of playground surfaces (12), said apparatus comprising:
    a drop module (14);
    release means (16) for holding said drop module (14) at an elevated reference height and releasing said drop module (14) to fall to the surface (12);
    a guide element (18) extending between a guide element upper end (20) and a guide element lower end (22) in an operational configuration for guiding and maintaining said drop module (14) in a constant attitude from release until surface (12) impact;
    a support structure (24) extending between said upper (20) and lower (22) ends of said guide element (18) in an operational configuration for holding said guide element (18) in a generally vertical orientation above the surface (12);
    conversion means for converting each of said support structure (24) and said guide element (18) between said operational configuration for surface-testing and a compact configuration for convenient transport; and
    said support structure comprising generally vertical segments (26, 28, 30) compressively held together by said guide element (18) in said operational configuration.

2. An apparatus (10) as set forth in claim 1 where said conversion means includes connections (31) between said vertical segments (26, 28, 30) to form generally vertical rods (32) in said operational configuration.

3. An apparatus (10) as set forth in claim 2 where said support structure (24) includes leg segments (36) releasably connected to said vertical rods (32) in said operational configuration and extending diagonally outward and downward.

4. An apparatus (10) as set forth in claim 3 where said support structure (24) includes upper horizontal segments (38) extending between and releasably connected to said vertical rods (32) in said operational configuration.

5. An apparatus (10) as set forth in claim 4 where said support structure (24) includes lower horizontal segments (40) extending between and releasably connecting to said legs (36) in said operational configuration.

6. An apparatus (10) as set forth in claim 5 where said vertical (26, 28, 30), horizontal (38, 40) and leg (36) segments comprise tubular steel.

7. An apparatus (10) as set forth in claim 2 where said vertical rods (32) are disposed generally parallel to one another and rigidly and are releasably connected to a top plate (42) and a bottom plate (44) in said operational configuration.

8. An apparatus (10) as set forth in claim 7 where said top plate (42) and bottom plate (44) comprising flat annular steel plates.

9. An apparatus (10) as set forth in claim 7 where said guide element (18) comprise two flexible elongated members (64) extending from said top plate (42) to said bottom plate (44) in said operational configuration.

10. An apparatus (10) as set forth in claim 9 where said flexible elongated members (64) include tightening means (66) for tensioning and straightening said flexible elongated members (64).

11. An apparatus (10) as set forth in claim 10 where said flexible elongated members (64) comprise cables.

12. An apparatus (10) as set forth in claim 9 where said drop module (14) includes a headform (68).

13. An apparatus (10) as set forth in claim 12 where said headform (68) includes a linear accelerometer transducer (15).

14. An apparatus (10) as set forth in claim 13 where said drop module (14) includes two loose guide tubes (80) each slidably disposed around one of said flexible elongated members (64).

15. An apparatus (10) as set forth in claim 14 where said release means (16) includes a pulley (82) rotatably attached to said top plate (42).

16. An apparatus (10) as set forth in claim 15 where said release means (16) includes a mechanical release (84) disposed on said support structure (24).

17. An apparatus (10) as set forth in claim 16 where said release means (16) includes a rope (86) disposed over said pulley (82) with a first end (88) releasably engaging said mechanical release (84) and a second end (90) connected to said drop module (14).

18. An apparatus (10) as set forth in claim 1 where said conversion means include pinned joints (46, 48).

19. An apparatus (10) as set forth in claim 18 where each of said pinned joints (46, 48) includes a quick release pin (58) removably installed in quick-release pin hole (56) in said operational configuration.

* * * * *